(12) United States Patent
Bou Aoun et al.

(10) Patent No.: US 11,813,157 B2
(45) Date of Patent: Nov. 14, 2023

(54) NON-FOLDABLE POUCH FOR FORMING AN IMPLANTABLE ARTIFICIAL ORGAN

(71) Applicant: Defymed, Strasbourg (FR)

(72) Inventors: Richard Bou Aoun, Strasbourg (FR); Charles-Thibault Burcez, Strasbourg (FR); Jordan Magisson, Strasbourg (FR); Séverine Sigrist, Strasbourg (FR)

(73) Assignee: DEFYMED, Strasbourg (FR)

( * ) Notice: Subject to any disclaimer, the term of this patent is extended or adjusted under 35 U.S.C. 154(b) by 825 days.

(21) Appl. No.: 16/630,176

(22) PCT Filed: Jul. 10, 2018

(86) PCT No.: PCT/EP2018/068711
§ 371 (c)(1),
(2) Date: Jan. 10, 2020

(87) PCT Pub. No.: WO2019/011939
PCT Pub. Date: Jan. 17, 2019

(65) Prior Publication Data
US 2020/0146802 A1    May 14, 2020

(30) Foreign Application Priority Data
Jul. 10, 2018   (EP) ..................... 17305922

(51) Int. Cl.
*A61F 2/02*   (2006.01)
*C12M 1/00*   (2006.01)
*A61L 27/06*   (2006.01)
*A61L 27/56*   (2006.01)

(52) U.S. Cl.
CPC ............. *A61F 2/022* (2013.01); *C12M 23/14* (2013.01); *A61L 27/06* (2013.01); *A61L 27/56* (2013.01)

(58) Field of Classification Search
CPC ........... A61F 2/022; A61F 2/04; C12M 23/14; A61L 27/06; A61L 27/56
See application file for complete search history.

(56) References Cited

U.S. PATENT DOCUMENTS

| 9,669,154 B2 | 6/2017 | Wahlberg |
| 2013/0216746 A1 | 8/2013 | Piranda |
| 2013/0261543 A1 | 10/2013 | Wahlberg et al. |
| 2017/0232186 A1 | 8/2017 | Wahlberg |

FOREIGN PATENT DOCUMENTS

| EP | 2621403 B1 | 8/2013 |
| WO | WO 2008/079997 | 7/2008 |
| WO | WO 2012/041320 | 4/2020 |

*Primary Examiner* — Yashita Sharma
(74) *Attorney, Agent, or Firm* — Panitch Schwarze Belisario & Nadel LLP; Erin M. Dunston

(57) ABSTRACT

The present invention relates to an implantable pouch which contains a rigid plate in its inner volume, thereby preventing said pouch to be folded.

17 Claims, 2 Drawing Sheets

A.

B.

NON-FOLDABLE POUCH FOR FORMING AN IMPLANTABLE ARTIFICIAL ORGAN

CROSS-REFERENCE TO RELATED APPLICATIONS

This application is a U.S. National Stage Application pursuant to 35 U.S.C. § 371 of International Patent Application PCT/EP2018/068711, filed on Jul. 10, 2018, and published as WO 2019/011939 on Jan. 17, 2019, which claims priority to European Patent Application 17305922.1, filed on Jul. 12, 2017, all of which are incorporated herein by reference in their entireties for all purposes.

FIELD OF THE INVENTION

The present invention relates to a pouch for forming an implantable artificial organ such as a pancreas, which contains a rigid plate in its inner volume, thereby preventing said pouch to be folded.

BACKGROUND

The treatment of pathological conditions requiring a continuous supply, to the body, of substances of interest has made necessary the development of devices which can be implanted in a patient and are capable of releasing these substances efficiently and sometimes for long periods of time.

To satisfy this need, bioartificial organs which contain cells producing one or more substances of interest have been developed. The cells contained in a bioartificial organ are confined in internal spaces, or encapsulating chambers, delimited by at least one semi-permeable membrane. Such a membrane is termed "semi-permeable" when it allows the diffusion of the substances of interest out of the encapsulating chamber to the target cells in the patient's body, while at the same time being impermeable to the antibodies and the cells of the patient's immune system, thus preventing them from directly attaching the cells producing the substance(s) of interest.

A bioartificial organ is understood to be a device, in particular intended to be implanted in a patient, comprising at least one chamber consisting of at least one permeable membrane.

Said chamber may intended contain cells which secrete one or more substance(s) of interest. In this case, the membrane is semi-permeable, in that it allows passage of substances of a size below a given threshold (typically substances secreted by the cells that go from the inside of the chamber to the body of the patients or nutrients that will feed the cells) and prevents entry within the chamber of molecules of a size above the selected threshold (typically cells or molecules of the immune system (such as cytokines or antibodies) that could destroy the cells within the chamber).

In another embodiment, a catheter would arrive within the chamber in order to deliver the compound of interest within the chamber, the compound of interest being able to diffuse through the membrane to the patient's body. The membrane is also semi-permeable, in that only substances of a size below a given threshold can diffuse through the membrane. In this embodiment, though, the size of the threshold may be higher than in the case the chamber contains live cells. This makes it possible to have diffused a substance of a larger size, such as a protein.

A substance of interest is any substance intended to have a beneficial, in particular therapeutic, effect in the patient. This may therefore be a neurotransmitter, a hormone, a growth factor, a coagulation factor or a cytokine. In particular, such a substance may be, without any limiting nature, insulin, glucagon, growth hormone, coagulation factor IX, coagulation cofactor VIII or calcitonin. It can be, in particular, a growth hormone (for treating dwarfism), a coagulation factor (for treating hemophilia), a cytokine or the like (tumor-necrosis factors, interferons . . . ) or an anti-inflammatory molecule (whether nonsteroidal or steroidal) useful for treating auto-immune diseases such as arthritis, ankylosing spondylitis, multiple sclerosis, celiac disease, Graves disease, inflammatory bowel disease, psoriasis, rheumatoid arthritis, and systemic lupus erythematosus, heparin or heparinoids useful for treating coagulation, a compound used in immunotherapy, a drug used in chemotherapy, an immunosuppressing drug (such as for treating Graft vs Host rejections), an antiviral drug, arsenic (some auto-immune diseases), TNF (useful for hepatitis C), dopamine (for Parkinson disease treatment), eptifibatide (for reducing the risk of acute cardiac ischemic events and treating heart failure), a beta blocker drug.

Examples of devices (bioartificial organs, semi-permeable membranes, encapsulating chambers) are known in the prior art.

Mention may thus be made of WO 02/060409 which describes a membrane consisting of a porous polycarbonate biocompatible film which is surface-modified by generation of polar sites and covered with a layer of at least one hydrophilic polymer, and the use thereof for manufacturing bioartificial organs.

WO 2012/017337, US 2013/131828 and FR 2960783 describe a functionalized semi-permeable membrane composed of a porous biocompatible support pretreated so as to increase the surface energy thereof and comprising at least two layers, each comprising a hydrophilic polymer and at least one biologically active molecule, and also the use thereof in particular for manufacturing a bioartificial organ and an encapsulation chamber. The biologically active molecules disclosed in this application are VEGF and heparin, which is, in particular, present in a HPMC or EC layer.

WO 2012/010767 and US2013/0216746 describe a bag (or pouch or pocket) for forming an implantable artificial organ, which comprises a closed shell made of a semi-permeable membrane. This bag also comprises a sheet contained in the shell, the sheet comprising projections (protuberances) on the surface thereof for maintaining a space for cells between the sheet and the shell.

WO 2015/086550 describes a chamber for encapsulating secreting cells producing at least one substance of interest, comprising a closed shell made of a semi-permeable membrane, delimiting a space capable of containing said secreting cells producing at least one substance of interest, wherein said membrane comprises at least one layer of porous biocompatible polymer, and one layer of non-woven biocompatible polymer.

One can also cite FR 2 384 504 (disclosing an artificial pancreas), EP 664 729 (disclosing an implantable and refillable artificial pancreas).

Of interest is WO 94/18906, disclosing cells within an envelope made of a semi-permeable membrane, which envelope is contained in another container providing mechanical protection of the first envelope. The cells are, for example, thyroid cells, parathyroid gland cells, adrenal gland cells, liver cells or pancreas cells. The replacement of the cells requires complete replacement of the device.

WO 2008/079997 discloses a container suitable for implantation in a living body having an exterior wall portion and an interior wall portion, said exterior wall portion being permeable to materials of a greater size than said interior wall portion, wherein the container is supported interiorly with an interior support within the confines defined by the interior wall portion.

One problem for these implantable pouches is that the forces within the body may fold the pouches, thereby having a deleterious effect for the cells within the pouches, or even shearing and tearing apart the membranes leading to weakening or even breaking of the membranes.

Accordingly, there is a need for a pouch for forming an implantable artificial organ that remains resistant during and after implantation of the pouch.

SUMMARY OF THE INVENTION

The invention relates to a pouch (or shell) for forming an implantable artificial organ/device wherein said pouch is a closed envelope made from two semi-permeable membranes that are sealed all over the perimeter of the pouch, thereby defining an inner volume and an outer volume of the pouch, wherein said pouch contains a substantially plane rigid plate in its inner volume.

The two semi-permeable membranes forming the pouch are preferably heat-welded together. Use may be made of the method described in WO 2012/010767 or a method of heat-welding using ultrasound, known in the art. Membranes can also be sealed on their periphery, to form the chamber, using any other thermosealing method known in the art.

This method for forming the shell is simple and makes it possible to easily enclose the rigid plate within the shell. The pouch may comprise a frame covering the weld seam, such as a silicone frame although other material could also be chosen by the person skilled in the art. The frame prevents or inhibits the heat-sealed edges from aggravating the tissue surrounding the pouch.

The rigid plate (which may also be named "foil" or "sheet") is preferably made from a biocompatible material. In some embodiments, though, as the ones where it is embedded within an elastomer, it could be made of a material that is not biocompatible.

It is recalled that the term "biocompatible" is said of a material which is well tolerated by a living organism and which does not cause a rejection reaction, a toxic reaction, a lesion or a harmful effect on the biological functions of the latter. This does not exclude the possibility of an inflammatory reaction due to the insertion of the material into the organism or of an immune reaction in the case of a biocompatible organ comprising exogenous cells; this immune reaction is not therefore due to the organ as such, but instead due to its content (secretion of chemokines by the exogenous cells). ISO 10993 standard entails a series of sections for evaluating the biocompatibility of medical devices.

Semi-Permeable Membrane

The membrane forming the pouch is semi-permeable, indicating that it presents a cut-off threshold, the molecules having a weight above this cut-off threshold being unable to cross the membrane, while the molecules having a weight below this cut-off threshold can cross the membrane. The determination of the cut-off threshold is carried out by those skilled in the art according to the characteristics of the molecules that they wish to stop or allow to penetrate.

In one preferred embodiment, and in order to allow the passing of small molecules such as insulin, glucagon or glucose and to stop the effector molecules of the immune system (such as antibodies and complement factors), this cut-off threshold is between 40 kDa and 500 kDa, or between 100 kDa and 500 kDa, or between 100 kDa and 150 kDa, more preferably between 50 kDa and 150 kDa.

The internal diameter of the pores of the porous polymer makes it possible to obtain the desired cut-off threshold. Thus, in one particular case, the internal diameter of the pores present on the layer of porous biocompatible polymer is between 5 and 100 nm, entirely preferably between 5 and 50 nm.

DETAILED DESCRIPTION OF THE INVENTION

Dimensions of the Plate

It is preferred when the dimensions of the rigid plate are big enough so that the plate is constraint in its moves and remains substantially parallel to the membranes forming the pouch. This may be achieved when the surface of the rigid plate is at least 60% 70%, 75% or 80% of the surface of the pouch (i.e. the surface of a membrane). For 60%, this would correspond to a diameter being about 77% of the diameter of the pouch. Consequently, for a pouch with a 10 cm diameter, the plate would have a 7.7 cm diameter, thus leaving an annulus of a little more than 1 cm between the plate and the side of the pouch. Such dimensions would thus achieve the technical effect of preventing folding of the pouch.

In such embodiment, this ensures that the rigid plate is able to prevent the folding of the pouch in response to forces exerted by the organs after implantation.

As an illustration, when the pouch (and thus the plate) is circular, the diameter of the plate is thus at least 70%, preferably at least 75% the diameter of the pouch, preferably at least 77.5% the diameter of the pouch, more preferably at least 80% the diameter of the pouch, or at least 85% the diameter of the pouch or at least 90% the diameter of the pouch.

In particular when the plate is embedded in a biocompatible elastomer (see below), the surface of the rigid plate is at least 80% of the surface of the biocompatible elastomer, but may also be at least 85% of the surface of the biocompatible elastomer, or even at least 90% of the surface of the biocompatible elastomer.

When the pouch has another shape (such as square or rectangular), the plate surface shall preferably have the same shape than the pouch.

The Plate and Pouch are Substantially Flat

One can consider that the pouch according to the invention is substantially flat and defines a plan.

One can say that the pouch thus obtained is substantially plane (flat). That is to say that the dimensions of the pouch in the (x,y) plan (parallel to the plan of the plate) are substantially bigger than the dimensions along the (z) axis (perpendicular to the (x,y) plan).

This is because the membranes and the rigid plate are substantially flat and their height is substantially lower than their length and width.

Indeed, the thickness of a membrane is generally between 45 and 250 μm.

The thickness of the plate is advantageously comprised between 0.01 mm and 2 mm, preferably between 0.05 mm and 1 mm or 0.05 mm and 0.6 mm or 0.1 mm and 1 mm or 0.1 mm and 0.6 mm.

The total thickness of the pouch is thus generally around 1.5 mm at the most.

In contrast, the dimensions of the chamber (defined by the dimensions of the membrane) are:

When the chamber (pouch) is circular, the diameter of the encapsulating chamber is preferably greater than 3 cm, preferably greater than 5 cm, or than 8 cm. It is generally less than 20 cm, and is preferentially less than 15 cm, or than 14 cm. A diameter of between 8 and 14 cm is perfectly acceptable.

When the chamber is not round, the largest dimension thereof is generally greater than 3 cm, preferably greater than 5 cm, or than 8 cm. It is generally less than 20 cm, and is preferentially less than 15 cm, or than 14 cm.

Consequently, the largest dimension of the chamber in the (x,y) plan is generally more than 20 times higher than the largest dimension along the (z) axis and the pouch may be, for purpose of simplification, qualified as being plane in the plan defined by its largest dimensions.

The technical role of the rigid plate is to make it possible to prevent folding in response to forces that would apply substantially within the (x,y) plan on the pouch at the site of implantation. In fact, the scaring around the pouch after implantation is a crucial time when the pouch is submitted to various strengths and has the most risk to be folded in the absence of the rigid plate. Although the plate may slightly bend (a 5% deformation may be accepted, corresponding to a difference of height of 5 mm between the two extremities of the diameter in case of a plate with a 100 mm diameter), the rigidity of such plate will ensure maintenance of the substantially planar shape of the pouch.

This property may be verified by X-rays or scanner, this method being preferred. The substantially planar rigid plate may be maintained within the pouch, by using a traversing pin or the like that links the upper and lower membranes thus going through the plate and secured on the upper and lower membrane. This would thus prevent movement of the plate on the (x,y) plane within the pouch.

Thickness of the Plate

The thickness of the plate can be determined and adapted by the person skilled in the art, in particular to ensure that the plate will perform its intended purpose (to avoid folding of the pouch). The plate should thus not fold by itself. The thickness of the plate may depend of the hardness of the material that is used and can easily be optimized by the person of skill in the art. When the plate is made with titanium, the thickness of the plate is thus generally comprised between 0.01 mm and 2 mm, preferably between 0.05 mm and 1 mm or between 0.05 mm and 0.6 mm or between 0.1 mm and 1 mm or between 0.1 mm and 0.6 mm. it thus appears that the thickness is generally greater than 0.01 mm, preferably greater than 0.05 mm, or greater than 0.1 mm. The thickness is generally lower than 1 mm or lower than 0.8 mm or may even be lower than 0.6 mm.

It is however to be noted that the thickness of the plate may be greater than the above-mentioned dimensions, or lower than these.

Material of the Plate

In a preferred embodiment, the plate is made of a material selected from the group consisting of a biocompatible metal, a biocompatible alloy and a biocompatible plastic.

A preferred biocompatible metal is titanium, and the plate may be made of titanium only, or from an alloy containing titanium, such as nitinol metal, an alloy of nickel and titanium, where the two elements are present in roughly equal atomic percentages.

In particular, rather than being in a plain material, the plate is made of a porous biocompatible material, in particular porous titanium. Methods for making porous titanium are known in the art (such as in US2009253099 or other documents).

In another embodiment, one makes use of a biocompatible thermoplastic, such as polyamide-6, la polyamide-6.6, polybutylene terephthalate, polyphtalamide, polyphenylene sulfide, polyether ether ketone (PEEK) or polypropylene.

In a specific embodiment, the plate is a lattice of the biocompatible material, or a mesh made from the biocompatible material.

Smooth or Not

In a specific and preferred embodiment, the surface of the plate is smooth. This embodiment would, in particular reduce the risk of damaging the membranes In another embodiment, the surface of the plate is not smooth. In this embodiment, the surface of the plate presents dips and rises. In this embodiment, the height of these dips and rises on the surface of the plate will be higher than 0.5 micrometer, or higher than 1 micrometer, or can also be higher than 2 micrometers.

In a specific embodiment, the plate presents, at its surface, larger protuberances, that make it possible to maintain a space for cells between the sheet and the envelope.

This embodiment is preferred when the artificial organ (the pouch) is intended to host live cells, so that they can be maintained entire surface of the plate without being compressed by the envelope against the plate. This would also make it possible to avoid formation of big cell aggregates and maintain a large exchange surface between the cells and the medium within the pouch, thereby guaranteeing prolonged viability and ability to produce the substance of interest.

The plate will preferably comprise protuberances on both of its faces.

As in U.S. Pat. No. 8,834,979, the protuberances may have the shape of dashes spaced apart from one another and forming regularly distributed lines parallel to one another. This arrangement defines channels in the direction in which the fluids may easily circulate, channels being oriented, for some, in the direction of the dashes, and, for others, obliquely with respect to said dashes.

In another embodiment, the protuberances are in staggered rows, thus creating channels that form parallel lines perpendicular to other parallel lines.

The width of the channels is in the order of 2 mm so as to avoid cell debris to be blocked within the channels.

In this embodiment, the height of these protuberances on the surface of the plate will be higher than 100 micrometers, or higher than 200 micrometers, or can also be as high as 300 micrometers.

In a specific embodiment, the edges of the plate are rounded. To round the edges may limit the sharpness of the edges and avoid any risk that the edges of the plate would pierce or tear apart the membranes of the pouch.

Holes

In a specific embodiment, the surface of the plate (and of the elastomer covering the plate) bears one or more holes. These holes make it possible to have communication between the two volumes determined by the plate within the pouch, and in particular to allow the any liquid and/or nutriments useful for maintaining viability and of the cells present in the pouch to circulate within the pouch.

Such hole(s) are also of interest to allow easy emptying and refilling of the pouch, for instance to change the cells within the pouch. Indeed, when a membrane forming the pouch comprises connectors such as disclosed in WO 2012/010767 (U.S. Pat. No. 8,834,979) that are used to empty the pouch of the cells and refill it, it is desirable that the pouch is entirely emptied before being refilled and that refilling leads to the cells being evenly distributed within the pouch. This is made more reliable by the presence of the holes.

Holes in the plate may also be crossed by rods that are attached to the membranes, thus limiting the movements of the plate within the pouch.

Elastomer

In a specific embodiment, the surface of the plate is covered with a biocompatible elastomer. In this embodiment, a layer of the biocompatible elastomer can be deposited on one side, or both sides of the plate.

It is, however, considered and preferred when the plate is embedded within the biocompatible elastomer.

In order to obtain a rigid plate coated with a biocompatible elastomer, one can:

(a) Provide a rigid plate (b) Mold the biocompatible elastomer over said rigid plate thereby obtaining a rigid plate coated with (embedded within) a biocompatible elastomer.

In this embodiment, it is preferred when the rigid plate is made of biocompatible metal or alloy, preferably titanium or titanium alloy, and the biocompatible elastomer is silicone.

Such method is also part of the invention.

When molding the elastomer over the rigid plate, one can secure the plate in the mold with two barbs such as metallic barbs, to avoid it moving when the elastomer is added. In this embodiment, the plate shall thus present hole that have not been filled with the elastomer.

The plate can also present other holes that will be filled with the elastomer. Further holes are then pierced within the elastomer layer.

In a preferred embodiment, there are protuberances on the surface of the layer of the biocompatible elastomer. The elastomer (in particular silicone) coat thus presents, at its surface, protuberances, so as to maintain a space for cells between the sheet and the envelope.

The shape and disposition of the protuberances on the silicone layer are described above and in U.S. Pat. No. 8,834,979.

Surface Treatment

The surfaces of the plate (or elastomer coated) may be further covered by ways of surface treatment, in particular as to avoid cell adhesion thereon.

This surface treatment is preferably a hydrophilic and anti-adhesive treatment, with an appropriate hydrophilic polymer.

An hydrophilic polymer is a polymer or a blend of polymers, which, after application on the plate or elastomer, has a contact angle value of less than 40°, preferably less than 30°, after measurement according to the "sessile drop" test described in Example 2 of WO 02/060409.

Preferably, the hydrophilic polymer material is chosen from the following hydrophilic polymers:

celluloses and derivatives thereof, such as ethylcellulose (EC), hydroxypropylmethylcellulose (HPMC) or carboxymethylcellulose (CMC);

polyacrylamides and copolymers thereof;

polyvinylpyrrolidone (PVP) and copolymers thereof;

polyvinyl alcohols;

vinyl acetate copolymers, such as a poly(vinyl acetate)/poly(vinyl alcohol) copolymer;

polyethylene glycols;

propylene glycols;

hydrophilic poly(meth)acrylates;

polysaccharides;

chitosans.

One can use a single polymer or a blend of several of the hydrophilic polymers above, generally a blend of two or three of the hydrophilic polymers above.

Preferably, the hydrophilic polymer is chosen from cellulose-based compounds, in particular HPMC, EC, TEC or CMC, polyvinylpyrrolidones, poly(vinyl alcohol)s, or polyacrylates such as poly(hydroxyethyl acrylate) (HEA) or acrylic acid copolymers.

The hydrophilic polymer may also be composed of a blend of two or more hydrophilic polymers mentioned above, in particular a blend of HPMC and CMC, or of HPMC and EC.

Celluloses and cellulose derivatives, in particular hydroxypropylmethylcellulose (HPMC), are preferred.

In particular, the silicone coat may have a surface treatment of the SI-HPMC-CMC type. SI refers to silicone, HPMC refers to hydroxypropyl-methylcellulose and CMC refers to carboxymethyl cellulose.

Manufacture of the Pouch

The invention also relates to a method for manufacturing a pouch as herein described, comprising the steps of (a) Providing a first semi-permeable membrane (b) Putting a rigid plate as described herein on the top of said first membrane (c) Putting a second semi-permeable membrane on the top of said plate (d) Sealing the two semi-permeable membranes, thereby obtaining a pouch which is a closed envelope made from the two semi-permeable membranes, said pouch containing the rigid plate in its inner volume. The membranes can be sealed by heat-welding as described above.

Membranes

The semi-permeable membranes are made from one or more layer of biocompatible polymer(s), with at least one layer that is porous, in order to control the size of the molecules that can cross the membranes.

Material

Such membranes are disclosed in particular in WO2016184872 and WO2015086550.

In particular, the membranes comprise at least one layer of porous biocompatible polymer, and one layer of non-woven biocompatible polymer.

Porous biocompatible polymers are known in the art. It may be chosen from polycarbonate (PC), polyester, polyethyleneimine, polypropylene (PP), poly(ethylene terephthalate) (PET), poly(vinyl chloride) (PVC), polyamide and polyethylene (PE), polyether sulfone (PES).

In one particular embodiment, at least one layer or more layers, as appropriate, is (are) made of poly(ethylene terephthalate) (PET).

As indicated, and for greater mechanical stability, the porous biocompatible polymer membrane may be reinforced by a membrane made of non-woven. The combination of a non-woven polymer and of the porous membrane of biocompatible polymer is preferentially carried out by lamination, using methods known in the art, such as thermal lamination, with or without the presence of adhesives, preferably without adhesive.

In a specific embodiment, the membrane consists of two layers of porous biocompatible polymer surrounding a layer of non-woven.

It is recalled that a non-woven polymer (non-woven) is such that the fibers thereof are maintained randomly. It is thus a sheet consisting of fibers oriented in a particular direction or randomly, bonded by friction and/or cohesion and/or adhesion. The fibers are thus arranged statistically, i.e. deposited randomly. Consequently and due to the random arrangement of the fibers, the non-woven polymer is permeable to substances, and there is no control of the size of the substances that can diffuse within the non-woven polymer. Non-woven polymers can be produced using polymeric fibers of any type. Mention may thus be made of polyesters: PET (poly(ethylene terephthalate)), PBT (poly (butylene terephthalate)), PVC (poly(vinyl chloride)), PP (polypropylene), PE (polyethylene) or blends of these polymers.

It is also to be noted that, without the treatment to make a biocompatible polymer porous, such polymer would remain impervious to any substance, and would not allow diffusion of the substance of interest from the inner part of the biocompatible organ to the outer part. The pores only allow the diffusion of substances that are below the cutoff (i.e. that are smaller than the pore diameter).

Pore Density and Size

Pore densities and sizes are disclosed in particular in WO2016184872 and WO2015086550.

Pore density is generally greater than $10^6$ pores/cm$^2$, preferably greater than $10^7$ pores/cm$^2$. This pore density is generally less than $10^{11}$ pores/cm$^2$, preferably less than $10^{10}$ pores/cm$^2$. Use is therefore made of membranes which can have a pore density preferentially greater than $10^6$ pores/cm$^2$, more preferably greater than $10^7$ pores/cm$^2$. This density is preferentially less than $10^{11}$ pores/cm$^2$, or even less than $10^{10}$ pores/cm$^2$. This density is therefore between $10^6$ pores/cm$^2$ and $10^{11}$ pores/cm$^2$. A density greater than $10^9$ and less than $10^{10}$ pores/cm$^2$ is perfectly suitable.

At least one of the two layers (or the only layer if such is the case) of porous biocompatible polymer has pores which have an internal diameter greater than 5 nm and preferably greater than 10 nm, and less than 100 nm, and preferably greater than 10 nm and less than 50 nm, more preferably less than 40 nm. It has also been observed that a pore diameter of less than 90 nm at the surface of the membrane is also very favorable for this layer of porous biocompatible polymer, as such pore diameter maintains the semi-permeability property, that is sought for the membrane. The pore density is then advantageously greater than $2.10^9$ and less than $4.10^{10}$ pores/cm$^2$.

When the membrane has two layers of porous biocompatible polymers, the internal diameter of the pores of one of the layers is preferentially as above.

The internal diameter of the pores of the second layer may be larger, the cut-off effect at the desired size being given by the diameter of the pores of the first layer. Thus, the internal diameter of the pores of the second layer may be greater than 100 and less than 2000 nm, preferably greater than 200 nm. These pores preferably have an internal diameter less than 1000 nm. An internal pore diameter greater than 400 and less than 600 nm, or of approximately 500 nm, is perfectly suitable. The pore density is then advantageously greater than $5.10^6$ and less than $5.10^7$ pores/cm$^2$.

When the membrane comprises two layers of porous biocompatible polymer, which surround the layer of non-woven, it is preferable for the encapsulating chamber to be such that the layer for which the pore diameter is the smallest is situated inside the chamber (in contact with the secreting cells producing at least one substance of interest) and that the layer for which the pore diameter is the widest is situated on the outside (in contact with the patient's body).

Thickness of the Membranes

When the membrane comprises only one layer of porous biocompatible polymer, the thickness of the membrane is preferably higher than 5 µm and lower than 250 µm, and more preferably comprised between 5 µm and 200 µm, or between 5 µm and 50 µm.

When the membrane is made of various layers of biocompatible polymers, such as non-woven and porous biocompatible polymers, the thickness of the membrane is preferably as disclosed in WO2016184872 and WO2015086550.

In particular, the total thickness of the membrane (comprising the layer of non-woven polymer and the layer(s) of porous polymer(s)) is greater than 45 µm. It is generally, and preferably, less than 250 µm, but can also be greater than this size; thicknesses ranging up to 300 µm, or even beyond, can in particular be envisaged.

Preferably, it is greater than 50 µm. It is also preferentially less than 150 µm. This membrane thus generally has a thickness of between 45 and 250 µm.

The layer of non-woven polymer generally has a thickness greater than 40 µm, preferably greater than 60 µm, more preferably greater than 80 µm. This layer has a thickness generally less than 250 µm and preferably less than 150 µm. Thus, the thickness of the layer of non-woven polymer is often between 40 µm and 150 µm. In this embodiment, and when the membrane has only one layer of biocompatible polymer, said layer then has a thickness greater than 5 µm. This layer is less than 250 µm, preferably less than 100 µm, being, however, preferably less than 50 µm. When the membrane has two layers of porous biocompatible polymer, these layers may have the same thickness. In another embodiment, said layers have different thicknesses. It is then preferred when the thickness of the inner layer is greater than 5 µm. It is also preferably less than 250 µm, but preferably less than 40 µm; a thickness less than 15 µm (and preferably greater than 5 µm) is perfectly suitable. The thickness of the second (outer) layer is generally greater than 25 µm. It is preferably less than 250 µm, preferably less than 100 µm, more preferably less than 50 µm; a thickness of between 30 and 50 µm is perfectly suitable.

Shape of the Chamber

In one preferred embodiment, the encapsulating chamber is circular, as this shape lacks "corners" or protruding parts, capable of creating cell or inflammatory aggregates during the implantation, and is easy when manufacturing the encapsulating chamber (no need to orient the two membranes and the plate).

In one particular embodiment, the diameter of the encapsulating chamber is greater than 5 cm, preferably greater than 8 cm. It is generally less than 20 cm, and is preferentially less than 15 cm, or than 14 cm. A diameter of between 5 and 14 cm is perfectly acceptable.

When the chamber is not round, the largest dimension thereof is generally greater than 3 cm, preferably greater than 5 cm, or than 8 cm. It is generally less than 20 cm, and is preferentially less than 15 cm, or than 14 cm.

Volume of the Chamber and Cells

As seen above, the encapsulating chamber preferentially is intended to contain secreting cells producing at least one substance of interest, and to allow said cells to secrete this substance for a considerable period of time (greater than 3 months, preferentially greater than 6 months) at levels which are of physiological interest (i.e. making it possible to meet the patient's need).

The preferred internal volume of the encapsulating chamber should be greater than 15 ml, preferably greater than 20 ml, more preferably greater than 25 ml, and can rise to 50 ml, for use in humans.

Such encapsulating chambers must be able to contain a large number of cells. In the context of the treatment of diabetes, it must be possible to encapsulate the equivalent of at least 500 000 islets of Langerhans, preferably the equivalent of more than 700 000 islets, and optionally up to the equivalent of one million islets of Langerhans. In the knowledge that one islet contains, on average, about 1000 cells, this gives an estimation of the number of cells that the encapsulating chamber according to the invention can contain.

The number of cells will obviously vary according to the type of cells that it is desired to encapsulate and implant in the patient.

Preferred Embodiment

In one preferred embodiment, the membrane forming the encapsulating chamber comprises two layers of porous biocompatible polymers on either side of the non-woven polymer. In this embodiment, it is preferred for at least the internal layer (situated inside the chamber after formation of the chamber) to be the layer on which the pores provide the semi-permeable nature of the membrane (cut-off threshold), i.e. which has the pores that have an internal diameter greater than 5 nm (and generally less than 100 nm) or having the other dimensions mentioned above.

The layer external to the shell (in contact with the patient's tissues and cells) can have pores with a larger internal diameter, in particular greater than 100 nm, but preferably less than 2000 nm, or having the other dimensions mentioned above.

Connectors

According to another embodiment, the pouch comprises at least one connector. This connector may comprise a body attached to the plate, and a channel so as to be in hydraulic communication with the inside of the pouch. It is thus possible to fill or empty the pouch by connecting these connectors to flexible tubes.

Such connector is described in particular in U.S. Pat. No. 8,834,979 and may contain a base, the plate being clamped between the base and the body in order to attach the connector to the sheet.

In the preferred embodiment, the pouch comprises at least two connectors, and it is possible to establish circulation between the two connectors so as to ensure emptying of the pouch.

In one embodiment, the invention relates to a kit comprising an implantable subcutaneous port connected to the flexible tube so that the implantable subcutaneous port is in hydraulic communication with the inside of the pouch. The implantable subcutaneous port is a closed receptacle placed under the skin of a person or an animal and that can be accessed by a needle through the skin and a septum of the port. Thus, the contents of the pouch can be renewed usually without the skin being passed through by a conduit.

The invention also relates to a method of circulating a fluid within or from an implantable chamber comprising the step of circulating a fluid through a catheter linked to a connector attached to the chamber, which allows circulation of the fluid within or from the implantable chamber.

This method may be performed in vitro or in vivo when the chamber has been implanted. It is particularly adapted to empty the pouch of dead or inactive cells and refill it with new live cells. It is also adapted to deliver a substance of interest within the pouch for in situ diffusion through the membranes.

DETAILED DESCRIPTION OF AN EMBODIMENT OF THE INVENTION

Figure 1:
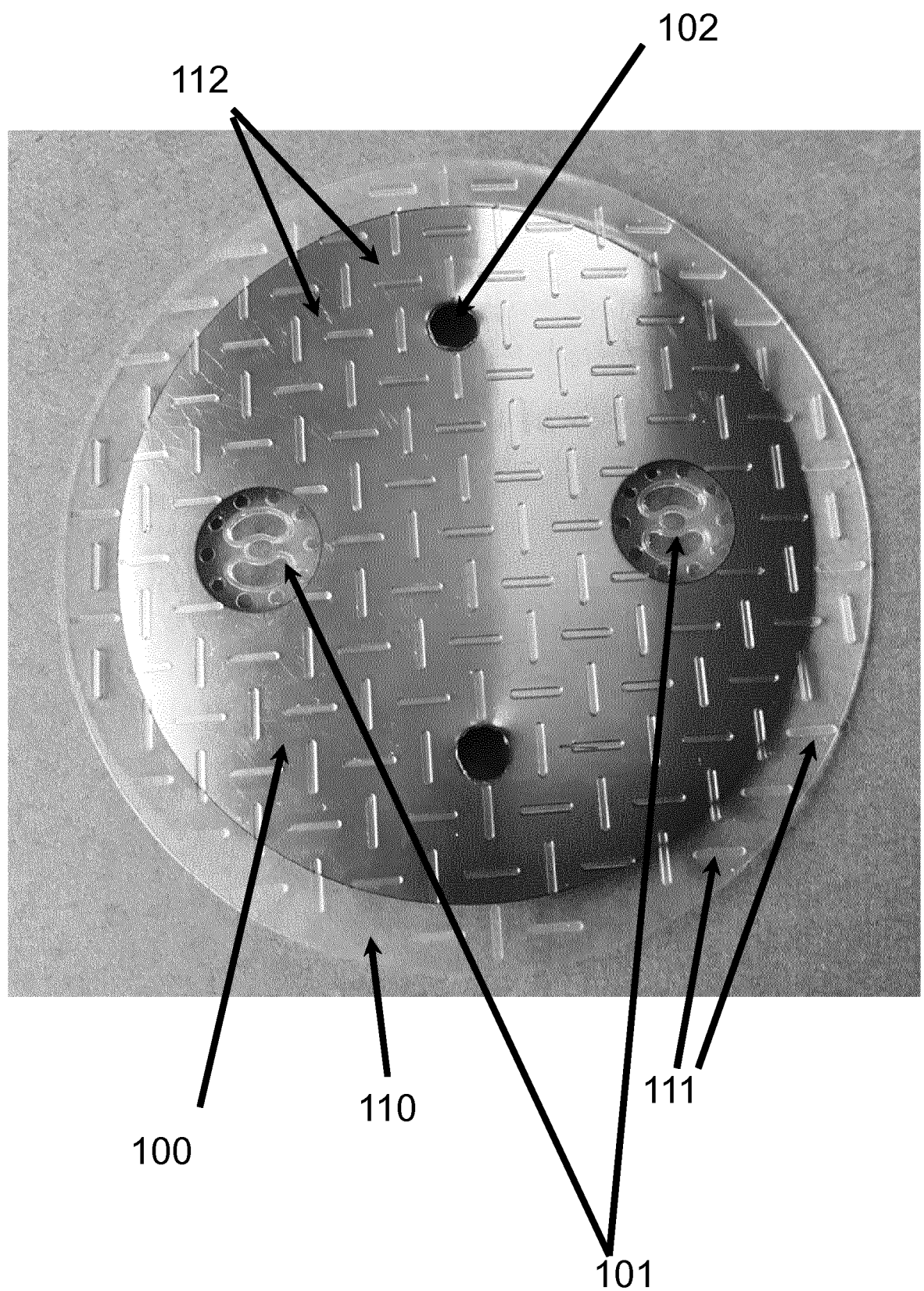
FIG. 1: upper view of a titanium sheet embedded in silicon according to one embodiment

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example" means that a particular feature, structure, or characteristic described is included in at least one embodiment described herein and does not imply that the feature, structure, or characteristic is present in all embodiments described herein.

FIG. 1 is a representation of a rigid plate intended to be associated to semi-permeable membranes for forming an implantable chamber which can be used for encapsulating secreting cells producing at least one substance of interest.

This plate (or plate), referenced 100 is herein disclosed as embedded within an elastomer (here silicon) layer 110.

The silicon layer comprises protuberances (111), that are in staggered rows, thus creating channels (112) in which the cells can settle.

The plate (100) further comprises holes (101, 102) that are useful for overmolding the silicon over the plate and allow communication of fluid between the two half-volumes delimited by the plate within the pouch. It can be seen that holes (101) have been pierced within the silicon layer, wherein holes 102 have not been filled with elastomer.

EXAMPLE

Example 1—Device Implantation in Pigs and Subsequent Retrieving

Landrace pigs were implanted with device with or without reinforcing plate.

Landrace pigs were implanted with device featuring implantable chambers described earlier or another system that is only placed on upper membrane.

Briefly, a premedication was performed by intramuscular injection of Azaperone (Stresnil®—2 mg/Kg) and Ketamine (Imalgene®–10 mg/Kg). Anesthesia was induced with intravenous injection of 0.4 mg/Kg of Propofol and completed by a muscle relaxant Pancuronium at 0.1 mg/Kg. Immediately after induction, an oro-tracheal intubation was performed and a pulmonary ventilation was set up using a semi-closed circular system connected on a respirator in a controlled-pressure mode. The maintenance of anesthesia was ensured on the inhalatory mode using isoflurane (inspired fraction=2 vol %) with a fresh gas debit of 2 L/min of a mixture of O2/N2O 50%/50% that serves as a vector gaz.

After shaving and disinfection of swine's abdomen, a midline incision was performed and a pouch was carefully dissected between the peritoneum and abdominal muscles. Device was then wetted with sterile saline solution and inserted into the pouch and attached at 4 points on abdominal muscles using 3/0 absorbable thread. Abdominal muscles and subcutaneous tissue were then sutured by simple overlock using 1/0 and 3/0 absorbable thread respectively.

Finally, skin was closed by intradermal suture using 3/0 absorbable thread. Animals were followed after surgery to ensure complete recovering of the animals with administration of Paracetamol (500 mg), Tramadol (50 mg) and Ketoprofen (50 mg) every 6 hours.

Once pre-determined implantation time is passed, pigs were anesthetized according to the same protocol as used for implantation. Device was retrieved and animals were sacrificed by injection of a lethal dose of potassium chloride.

Figure 2:
FIG. 2: implantable pouch after implantation and recovery without (A) or with (B) the presence of a rigid plate therein.
Figure 2:
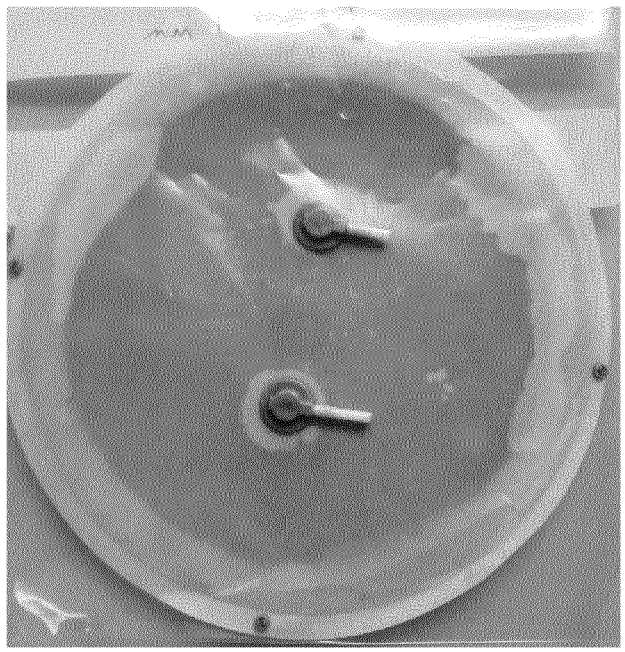

It is clear from FIG. 2 that the presence of the rigid plate within the pouch (FIG. 2.B) makes it possible to protect the shape of the pouch upon implantation wherein such pouch is torn in the absence of the plate (FIG. 2.A).

Example 2—Punching Test

Using a dedicated bench test, the device was tested with or without a titanium sheet overmolded with silicone. In this test, the device was a circle with a 120 mm diameter and the plaque was circular with a 96 mm diameter (corresponding to 80% of the device's diameter).

The test consists in a punching test with a penetration of 5 mm.

The test was performed at 37° C. in liquid solution.

When no titanium sheet present, the device could support 500 cycles, before breakage.

By comparison, when the device is reinforced with a titanium sheet, the device could achieve up to 7000 cycles.

In these "in vivo" mimicking conditions (at 37° C. in liquid), presence of a titanium plaque makes the device 14 times more resistant to punching.

The invention claimed is:

1. A pouch for forming an implantable artificial organ/device wherein said pouch is a closed envelope made from two semi-permeable membranes that are sealed all over the perimeter of the pouch, thereby defining an inner volume and an outer volume of the pouch, wherein said pouch contains a substantially planar rigid plate in its inner volume, wherein the rigid plate is made from a material selected from the group consisting of a biocompatible metal and a biocompatible alloy, wherein the rigid plate is made of titanium or of an alloy containing titanium.

2. The pouch of claim 1, wherein the rigid plate has the same shape as the pouch and the surface of the rigid plate is at least 60% of the surface of the pouch.

3. The pouch of claim 1, wherein the rigid plate has the same shape as the pouch and the surface of the rigid plate is at least 80% of the surface of the pouch.

4. The pouch of claim 1, wherein the surface of the plate is smooth.

5. The pouch of claim 1, wherein the surface of the plate is not smooth.

6. The pouch of claim 1, wherein the thickness of the plate is comprised between 0.01 mm and 2 mm.

7. The pouch of claim 1, wherein the surface of the plate bears holes.

8. The pouch of claim 1, wherein the plate is made of a porous biocompatible material.

9. The pouch of claim 1, wherein the surface of plate is covered with a biocompatible elastomer.

10. The pouch of claim 1, wherein the plate presents protuberances at its surface.

11. The pouch of claim 9, wherein the biocompatible elastomer is silicone.

12. The pouch of claim 1, wherein the plate surface is covered with a surface treatment as to avoid cell adhesion thereon.

13. The pouch of claim 1, wherein the alloy is nitinol.

14. The pouch of claim 1, wherein the porous biocompatible material is porous titanium.

15. The pouch of claim 11, wherein the silicone coat presents protuberances at its surface.

16. The pouch of claim 1, wherein the thickness of the plate is comprised between 0.1 mm and 0.6 mm.

17. The pouch of claim 9, wherein the elastomer coat surface is covered with a surface treatment as to avoid cell adhesion thereon.

* * * * *